US008652546B2

(12) United States Patent
Darien et al.

(10) Patent No.: US 8,652,546 B2
(45) Date of Patent: *Feb. 18, 2014

(54) MORINDA CITRIFOLIA BASED FORMULATIONS FOR REGULATING T CELL IMMUNOMODULATION IN NEONATAL STOCK ANIMALS

(75) Inventors: Benjamin J. Darien, Madison, WI (US); Richard G. Godbee, Saratoga Springs, UT (US)

(73) Assignee: Tahitian Noni International, Inc., Provo, UT (US)

( * ) Notice: Subject to any disclaimer, the term of this patent is extended or adjusted under 35 U.S.C. 154(b) by 312 days.

This patent is subject to a terminal disclaimer.

(21) Appl. No.: 12/199,369

(22) Filed: Aug. 27, 2008

(65) Prior Publication Data

US 2009/0068204 A1    Mar. 12, 2009

Related U.S. Application Data

(60) Provisional application No. 60/970,445, filed on Sep. 6, 2007.

(51) Int. Cl.
| A61K 36/00 | (2006.01) |
| A61K 36/73 | (2006.01) |
| A61K 39/00 | (2006.01) |
| A23K 1/17  | (2006.01) |
| A23K 1/165 | (2006.01) |

(52) U.S. Cl.
USPC ........ 424/777; 424/178.1; 424/725; 424/442; 424/765

(58) Field of Classification Search
None
See application file for complete search history.

(56) References Cited

U.S. PATENT DOCUMENTS

| 4,039,559 A | 8/1977 | Nakamura |
| 4,409,144 A | 10/1983 | Heinicke |
| 4,463,025 A | 7/1984 | Strobel |
| 4,543,212 A | 9/1985 | Heinicke |
| 4,666,606 A | 5/1987 | Heinicke et al. |
| 4,708,964 A | 11/1987 | Allen |
| 4,793,991 A | 12/1988 | Slimak |
| 4,948,785 A | 8/1990 | Nguyen |
| 4,996,051 A | 2/1991 | Meer et al. |
| 5,071,878 A | 12/1991 | Herschler |
| 5,106,634 A | 4/1992 | Thacker et al. |
| 5,110,803 A | 5/1992 | Nguyen |
| 5,213,836 A | 5/1993 | McGillivray et al. |
| 5,268,467 A | 12/1993 | Verbiscar |
| 5,275,834 A | 1/1994 | Thibault et al. |
| 5,288,491 A | 2/1994 | Moniz |
| 5,431,927 A | 7/1995 | Hand et al. |
| 5,472,699 A | 12/1995 | Duffy et al. |
| 5,503,825 A | 4/1996 | Lane |
| 5,565,435 A | 10/1996 | Yoneyama |
| 5,595,756 A | 1/1997 | Baily et al. |
| 5,616,569 A | 4/1997 | Reinhart |
| 5,717,860 A | 2/1998 | Graber et al. |
| 5,725,875 A | 3/1998 | Noll et al. |
| 5,731,356 A | 3/1998 | Jones et al. |
| 5,736,174 A | 4/1998 | Cooper et al. |
| 5,744,187 A | 4/1998 | Gaynor |
| 5,770,217 A | 6/1998 | Kutilek, III et al. |
| 5,776,441 A | 7/1998 | Scancarella et al. |
| 5,843,499 A | 12/1998 | Moreau et al. |
| 5,851,573 A | 12/1998 | Lepine et al. |
| 5,922,766 A | 7/1999 | Acosta et al. |
| 5,961,998 A | 10/1999 | Arnaud et al. |
| 5,962,043 A | 10/1999 | Jones et al. |
| 5,976,549 A | 11/1999 | Lewandowski |
| 6,029,141 A | 2/2000 | Bezos et al. |
| 6,039,952 A | 3/2000 | Sunvold et al. |
| 6,086,859 A | 7/2000 | Calello et al. |
| 6,086,910 A | 7/2000 | Howard et al. |
| 6,133,323 A | 10/2000 | Hayek |
| 6,136,301 A | 10/2000 | Pelle et al. |
| 6,139,897 A | 10/2000 | Goto et al. |
| 6,156,355 A | 12/2000 | Shields, Jr. et al. |
| 6,214,351 B1 | 4/2001 | Wadsworth et al. |
| 6,254,913 B1 | 7/2001 | Wadsworth et al. |
| 6,261,566 B1 | 7/2001 | Pillai et al. |
| 6,280,751 B1 | 8/2001 | Fletcher et al. |
| 6,291,533 B1 | 9/2001 | Fleischner |
| 6,299,925 B1 | 10/2001 | Xiong et al. |
| 6,387,370 B1 | 5/2002 | Yegorova |
| 6,405,948 B1 | 6/2002 | Hahn et al. |
| 6,417,157 B1 | 7/2002 | Wadsworth et al. |
| 6,436,449 B2 | 8/2002 | Gidlund |

(Continued)

FOREIGN PATENT DOCUMENTS

| CN | 1093919 | 10/1994 |
| CN | 1101256 | 4/1995 |

(Continued)

OTHER PUBLICATIONS

Herbal Remedies for Heart Disease. New Straits Times. Kuala Lampur : May 31, 2001 p. 5 (pp. 1-2 in ProQuest).*
Roeback et al. Effects of Chromium Supplementation on Serum High-Density Lipoprotein Cholesterol Levels in Men Taking Beta-Blockers. Annals of Internal Medicine. Dec. 15, 1991. vol. 115. Abstract.*
Mandasescu et al. Flaxseed Supplementation in Hyperlipidemic Patients. Rev med Chir Soc Med Nat Isai. Jul.-Sep. 2005; 109 (3). Abstract.*
Khan et al. Effect of Magnesium and Zinc on Antimicrobial Activities of Some Antibiotics. Pak J Pharm Sci. Oct. 2005; 18(4). Abstract.*
Triggiani et al. Role of Antioxidants, Essential Fatty Acids, Carnitine, Vitamins, Phytochemicals and Trace Elements in the Treatment of Diabetes Mellitus and Its Chronic Complications. Endocr Metab Immune Disord Drug Targets. Mar. 2006; 6(1). Abstract.*

(Continued)

*Primary Examiner* — Chris R Tate
*Assistant Examiner* — Russell Fiebig
(74) *Attorney, Agent, or Firm* — Michael F. Krieger

(57) ABSTRACT

Both liquid and dry form *Morinda citrifolia* enhanced animal food products are provided for increasing CD8$^+$ T cell activation in new born animals. Both contain *M. citrifolia* fruit puree and other *M. citrifolia* plant products.

6 Claims, No Drawings

(56) References Cited

U.S. PATENT DOCUMENTS

| | | |
|---|---|---|
| 6,477,509 B1 | 11/2002 | Hammons et al. |
| 6,528,106 B2 | 3/2003 | Wadsworth et al. |
| 6,589,514 B2 | 7/2003 | Jensen et al. |
| 6,737,089 B2 | 5/2004 | Wadsworth et al. |
| 6,749,875 B2 | 6/2004 | Selleck |
| 6,855,345 B2 | 2/2005 | Jensen et al. |
| 6,855,354 B2 | 2/2005 | Jensen et al. |
| 7,014,873 B2 | 3/2006 | West et al. |
| 7,018,662 B2 | 3/2006 | Jensen et al. |
| 7,033,624 B2 | 4/2006 | Jensen et al. |
| 7,048,952 B2 | 5/2006 | Gerson et al. |
| 7,070,813 B2 | 7/2006 | Jensen et al. |
| 7,122,211 B2 | 10/2006 | Jensen et al. |
| 7,144,439 B2 | 12/2006 | Isami |
| 7,186,422 B2 | 3/2007 | Jensen et al. |
| 2001/0033871 A1 | 10/2001 | Gidlund |
| 2002/0068102 A1 | 6/2002 | Su et al. |
| 2002/0090406 A1 | 7/2002 | Su et al. |
| 2002/0187168 A1 | 12/2002 | Jensen et al. |
| 2003/0060405 A1 | 3/2003 | Kleinman et al. |
| 2003/0086990 A1 | 5/2003 | Wang et al. |
| 2003/0108629 A1 | 6/2003 | Chou |
| 2003/0108630 A1 | 6/2003 | Story et al. |
| 2003/0108631 A1 | 6/2003 | Jensen et al. |
| 2003/0134001 A1 | 7/2003 | Jensen et al. |
| 2003/0134002 A1 | 7/2003 | Jensen et al. |
| 2003/0157205 A1 | 8/2003 | Jensen et al. |
| 2003/0206895 A1 | 11/2003 | Cavazza |
| 2003/0225005 A1 | 12/2003 | Gerson et al. |
| 2004/0086583 A1 | 5/2004 | Jensen et al. |
| 2004/0191341 A1 | 9/2004 | Palu et al. |
| 2004/0192761 A1 | 9/2004 | Palu et al. |
| 2004/0213862 A1 | 10/2004 | Su et al. |
| 2004/0224038 A1 | 11/2004 | Wang et al. |
| 2004/0244447 A1 | 12/2004 | Isami |
| 2004/0258780 A1 | 12/2004 | Woltering et al. |
| 2005/0037101 A1 | 2/2005 | Wang et al. |
| 2005/0075925 A1 | 4/2005 | Sash |
| 2005/0084551 A1 | 4/2005 | Jensen et al. |
| 2005/0106275 A1 | 5/2005 | Su et al. |
| 2005/0118291 A1 | 6/2005 | Wang et al. |
| 2005/0147700 A1 | 7/2005 | Jensen et al. |
| 2005/0158412 A1 | 7/2005 | Su et al. |
| 2005/0181082 A1 | 8/2005 | Isami et al. |
| 2005/0186296 A1* | 8/2005 | Palu et al. ............ 424/769 |
| 2005/0196476 A1 | 9/2005 | Zhou et al. |
| 2005/0202108 A1 | 9/2005 | Palu et al. |
| 2005/0202109 A1 | 9/2005 | Palu et al. |
| 2005/0260291 A1 | 11/2005 | Palu et al. |
| 2006/0088611 A1 | 4/2006 | Wang et al. |
| 2006/0141076 A1 | 6/2006 | Palu et al. |
| 2006/0159788 A1 | 7/2006 | West et al. |
| 2006/0193932 A1 | 8/2006 | Jensen et al. |
| 2006/0269630 A1 | 11/2006 | Palu et al. |
| 2006/0269631 A1 | 11/2006 | Su et al. |
| 2006/0275359 A1 | 12/2006 | Jensen et al. |
| 2006/0280818 A1 | 12/2006 | Palu et al. |
| 2007/0087066 A1 | 4/2007 | Gerson et al. |

FOREIGN PATENT DOCUMENTS

| | | |
|---|---|---|
| EP | 0555573 A1 | 8/1993 |
| EP | 0710450 A1 | 5/1996 |
| FR | 2673639 | 9/1992 |
| FR | 2783137 | 3/2000 |
| GB | 2253984 A | 9/1992 |
| JP | 355064504 | 5/1980 |
| JP | 61185167 | 8/1986 |
| JP | 62132829 | 6/1987 |
| JP | 06087736 | 3/1994 |
| JP | 06087737 | 3/1994 |
| JP | 8-208501 | 8/1996 |
| JP | 08208461 | 8/1996 |
| JP | 9-110688 | 4/1997 |
| JP | 11-43442 A | 2/1999 |
| JP | 2000095663 | 4/2000 |
| WO | 88/05304 A1 | 7/1988 |
| WO | 01/15551 A1 | 3/2001 |
| WO | 01/15553 A1 | 3/2001 |
| WO | 01/64231 A1 | 9/2001 |
| WO | 02/45654 A2 | 6/2002 |
| WO | 02/45734 A1 | 6/2002 |
| WO | WO2007084983 A * | 7/2007 |

OTHER PUBLICATIONS

Pazos et al. (2011) Natural Product Comm. vol. 6, No. 7, pp. 1005-1008.*
Office Action for U.S. Appl. No. 11/557,871 dated Mar. 14, 2008.
Office Action for U.S. Appl. No. 11/560,407 dated Feb. 7, 2008.
Office Action for U.S. Appl. No. 11/562,224 dated Jan. 30, 2008.
Office Action for U.S. Appl. No. 11/561,783 dated Jan. 30, 2008.
Office Action for U.S. Appl. No. 11/561,987 dated Feb. 7, 2008.
Office Action for U.S. Appl. No. 11/564,166 dated May 27, 2008.
Office Action for U.S. Appl. No. 11/613,820 dated Apr. 2, 2008.
Office Action for U.S. Appl. No. 11/620,914 dated Jan. 14, 2008.
Office Actions for U.S. Appl. No. 11/620,878 dated May 6, 2008 and Nov. 2, 2007.
Office Actions for U.S. Appl. No. 11/668,035 dated May 9, 2008 and Oct. 18, 2007.
Office Action for U.S. Appl. No. 11/682,355 dated Jun. 5, 2008.
Office Action for U.S. Appl. No. 11/686,451 dated Sep. 10, 2007.
Office Actions for U.S. Appl. No. 11/688,989 dated Mar. 28, 2008 and Oct. 3, 2007.
Office Actions for U.S. Appl. No. 09/983,282 dated Jun. 2, 2008 and Nov. 28, 2007.
Office Actions for U.S. Appl. No. 09/836,870 dated Jan. 24, 2006, Jun. 3, 2005, Nov. 4, 2004, May 6, 2004, Oct. 2, 2003, Mar. 25, 2003, Nov. 20, 2002, May 21, 2002 and Nov. 8, 2001.
Office Actions for U.S. Appl. No. 09/997,588 dated Jan. 10, 2008, Jul. 17, 2007, Jan. 24, 2007, Sep. 6, 2006, May 26, 2006, Dec. 21, 2005, Jun. 29, 2995, Dec. 1, 2004, May 4, 2004, Apr. 20, 2004, Dec. 18, 2003, May 20, 2003, Feb. 11, 2003, and Jun. 18, 2002.
Office Actions for U.S. Appl. No. 10/036,152 dated Feb. 12, 2004, Sep. 29, 2003 and Apr. 17, 2003.
Office Actions for U.S. Appl. No. 10/044,158 dated Oct. 2, 2003 and Jun. 20, 2003.
Office Actions for U.S. Appl. No. 10/124,627 dated Jul. 8, 2005, Mar. 11, 2005, Nov. 2, 2004, May 18, 2004, Dec. 24, 2003, Jun. 17, 2003, Jan. 28, 2003 and Oct. 1, 2002.
Office Actions for U.S. Appl. No. 10/294,089 dated Jun. 28, 2005, Dec. 28, 2004 and Apr. 1, 2004.
Office Actions for U.S. Appl. No. 10/286,112 dated Oct. 19, 2007, Mar. 12, 2007, Sep. 6, 2006, May 26, 2006, Dec. 6, 2006, Jun. 2, 2005, Nov. 2, 2004, Feb. 12, 2004, Sep. 23, 2003 and Jun. 3, 2003.
Office Actions for U.S. Appl. No. 10/285,359 dated May 26, 2005 and Feb. 13, 2004.
Office Actions for U.S. Appl. No. 10/335,653 dated Apr. 3, 2008, Sep. 7, 2007, Apr. 17, 2007, Nov. 11, 2006, Apr. 6, 2006 and Sep. 29, 2005.
Office Actions for U.S. Appl. No. 10/285,711 dated Apr. 30, 2008, Aug. 22, 2007, Mar. 27, 2007, Sep. 21, 2006, Apr. 6, 2006, Jun. 2, 2005, Oct. 21, 2004, Feb. 27, 2004 and Sep. 2, 2003.
Office Actions for U.S. Appl. No. 10/285,334 dated May 4, 2005 and Feb. 13, 2004.
Office Actions for U.S. Appl. No. 10/285,287 dated Jun. 5, 2008, Jan. 14, 2008, Aug. 16, 2007, Mar. 28, 2007, Oct. 23, 2006, Jun. 20, 2006, Feb. 16, 2006, Jul. 18, 2005, Mar. 9, 2005 and Sep. 7, 2004.
Office Action for U.S. Appl. No. 10/286,167 dated Mar. 22, 2004.
Office Actions for U.S. Appl. No. 10/396,868 dated Jun. 30, 2006, Jan. 12, 2006, Jul. 13, 2005, Jan. 11, 2005 and Aug. 13, 2004.
Office Actions for U.S. Appl. No. 10/808,872 dated Mar. 17, 2008, Aug. 9, 2007 and Jul. 31, 2006.
Office Actions for U.S. Appl. No. 10/798,730 dated Jan. 18, 2007, Jul. 31, 2006, Apr. 7, 2006 and Oct. 21, 2005.
Office Actions for U.S. Appl. No. 10/639,833 dated Oct. 18, 2007 and Sep. 21, 2006.
Office Actions for U.S. Appl. No. 10/417,406 dated May 5, 2008, Aug. 22, 2007, Jul. 13, 2006, Oct. 7, 2005 and Nov. 2, 2004.

(56) References Cited

OTHER PUBLICATIONS

Office Actions for U.S. Appl. No. 10/439,596 dated Jul. 15, 2005, Dec. 28, 2004 and Oct. 6, 2004.
Office Actions for U.S. Appl. No. 10/614,466 dated Apr. 3, 2006, Oct. 26, 2005, Jul. 1, 2005 and Dec. 29, 2004.
Office Actions for U.S. Appl. No. 09/839,433 dated May 21, 2008, Jun. 22, 2007, Mar. 27, 2006, Oct. 20, 2005, Apr. 22, 2005, Nov. 1, 2004, Apr. 20, 2004, Nov. 7, 2003, Apr. 4, 2003, Oct. 2, 2002 and Apr. 10, 2002.
Office Actions for U.S. Appl. No. 10/796,625 dated Jul. 13, 2006 and Sep. 23, 2005.
Office Actions for U.S. Appl. No. 10/862,828 dated Mar. 26, 2008 and Sep. 20, 2007.
Office Actions for U.S. Appl. No. 10/836,571 dated May 6, 2008, Jun. 20, 2007 and Jul. 31, 2006.
Office Action for U.S. Appl. No. 90/007,178 dated Apr. 21, 2005.
Office Actions for U.S. Appl. No. 10/937,419 dated Apr. 4, 2008, Oct. 31, 2007 and Jan. 25, 2007.
Office Actions for U.S. Appl. No. 10/948,815 dated Feb. 22, 2008, Sep. 7, 2007 and Feb. 22, 2008.
Office Actions for U.S. Appl. No. 11/034,505 dated May 1, 2008, Sep. 20, 2007 and Apr. 10, 2007.
Office Action for U.S. Appl. No. 11/091,051 dated Jan. 24, 2007.
Office Action for U.S. Appl. No. 10/993,883 dated Apr. 25, 2006.
Office Actions for U.S. Appl. No. 11/076,992 dated May 20, 2008, Nov. 16, 2007 and May 31, 2007.
Office Actions for U.S. Appl. No. 11/074,924 dated May 19, 2008, Nov. 15, 2007 and May 31, 2007.
Office Actions for U.S. Appl. No. 11/075,214 dated Jan. 14, 2008 and Apr. 23, 2007, Jan. 8, 2007 and Oct. 20, 2006.
Office Actions for U.S. Appl. No. 11/075,213 dated Apr. 23, 2008, Nov. 2, 2007 and Apr. 20, 2007.
Office Action for U.S. Appl. No. 11/216,418 dated May 4, 2007.
Office Action for U.S. Appl. No. 11/253,130 dated Dec. 19, 2006 and Aug. 4, 2006.
Office Actions for U.S. Appl. No. 11/257,681 dated Apr. 24, 2008 and Jul. 17, 2007.
Office Action for U.S. Appl. No. 11/360,550 dated Oct. 5, 2007.
Office Actions for U.S. Appl. No. 11/343,600 dated May 5, 2008 and Nov. 29, 2006.
Office Actions for U.S. Appl. No. 11/339,071 dated Jan. 10, 2008, Jul. 25, 2007 and Jan. 25, 2007.
Office Action for U.S. Appl. No. 11/376,066 dated Dec. 20, 2007.
Office Actions for U.S. Appl. No. 11/394,675 dated Apr. 14, 2008, Aug. 22, 2007 and Jun. 15, 2007.
Office Action for U.S. Appl. No. 11/438,547 dated Jan. 30, 2008.
Office Action for U.S. Appl. No. 11/438,553 dated Jan. 29, 2008.
Office Actions for U.S. Appl. No. 11/501,604 dated Jun. 5, 2008, Jan. 10, 2008 and Jul. 27, 2007.
Office Actions for U.S. Appl. No. 11/500,728 dated Jan. 29, 2008 and May 4, 2007.
Daulataba et al., "Ricinoleic acid in *Morinda citrifolia* seed oil," J. Oil Tech. Assoc. India (Mumbai, India) 21 (2):26-27 (1989).
Dittmar, Morinda, "Use in Indigenous Samoan Medicine," J. of Herbs, Spices & Medicinal Plants, 1(3):77-92 (1993).
El-Gammal et al., "Antimicrobial Activities of Some Flavonoid Compounds," Microbiol. 141:561-565 (1986).
Elkins, Hawaiian Noni, Woodland Publishing, pp. 6-31 (1998).
Farine et al., "Volatile Components of Ripe Fruits of *Morinda citrifolia* and Their Effects on *Drosophila*", Phytochemistry, 1996, pp. 433-438, vol. 41, No. 2.
Gagnon, D., "Liquid Herbal Drops in Everyday Use," 3d Ed., Bot. Res. Ed. Inst., p. 27 (1997).
Gura, "Systems for Identifying New Drugs are Often Faulty," Science 278:1041-1042 (1997).
Hirazumi et al.,"An Immunomodulatory Polysaccharide-Rich Substance from the Fruit Juice of *Morina citrifolia*(Noni) withAntitumorActivity,"Phytotherapy Research,13:380-387(1999).
Lampur, "Morinda achieves phenomenal sales of Tahitian noni juice", Malaysian Nat. News Agency Jul. 1999, p. 1.

Kimstra et al., "Foods of the Key deer," FL Sci., 53(4):264-273 (1990).
Levand et al., "Some chemical constituents of *Morinda citrifolia*," Planta Medica 36(2):186-187 (1979).
Liu et al., "2 Novel Glycosides from the Fruits of *Morinda citrifolia* (Noni) Inhibit AP-1 Transactivation & Cell Transformation in the Mouse Epidermal JB6 Cell Line," Cancer Res. 61:5749-5756 (2001).
Marona et al., "Pharmacological properties of some aminoalkanolic derivatives of xanthone," Pharmazie 56:567-572 (2001).
Morton, "The ocean-going noni, or Indian mulberry (*Morinda citrifolia*) and some of its 'colorful' relatives," Econ. Bot., 46(3):241-256 (192) 1992.
Mueller et al., "Noni Juice (*Morinda citrifolia*): Hidden Potential for Hyperkalameia?" Am H. Kidney Diseases., vol. 35, pp. 310-311 2000.
Mumford, L., "Benefits of Noni Juice may be Imagined; $30 Price Tag Isn't", So. Bend Tribune, So. Bend, Ind., pp. 1-2 (1998).
Naito, "Trace components in mulberry leaves," Nippon Nogei Kagaku Kaishi 42(7):423-425 (1968).
Peres et al., "Tetraoxygenated naturally occurring xanthones," Phytochemestry 55:683-710 (2000).
Product Alert. Oct. 11, 1999 29(19) PROMT Abstract.
Product Alert. Dec. 27, 1999 (29(24) PROMT Abstract.
Product Alert. Jun. 12, 2000 30(11) PROMT Abstract.
Rosenfeld, "Tropical Noni, a Tonic Boom; Nasty-Tasting Fruit Rockets onto the Health Product Market," Wash. Post; Aug. 7, 1997, p. C01:1-4 of Proquest.
Sang et al.,"Chemical Components in Noni Fruits and Leaves (*Morinda citrifolia* L.); Quality Management of Nutraceuticals,"Proceedings of Symposium,ACS,Wash.,DC pp. 134-150(2002.
Sang et al., "Flavonal Glycosides and Novel Irdoid Glycoside from the Leaves of *Morinda citrifolia*," J. Agric. Food Chem., 2001, 49(9) . pp. 4478-4481.
"Rachey Perry Environmental Skin Protector SPF 18," Product Alert, V.29(2) (1999).
Tahitian Noni Products (http://www.noni-now.com) (1998-2003).
Terumo Corp., "Anti-helicobacter pylor; Medicine Containing Extract of dried roots of *Morinda citrifolia* . . . " Database DWPI on West, An. 1996-439483 JP 08-217686—Japan (Aug. 1996).
Wang et al., "Novel Trisaccharide Fatty Acid Ester Identified from the Fruits of *Morinda citrifolia* (Noni)" J. Agric. Food Chem. 47(12):4880-7882 (1999).
Wang, Mingfu. "Chemical Components of Sage, Thyme and noni and their antioxidant and anticancer activities," Diss Abstr Int 2000 a B 61(1):13.
Webb, "Noni Juice Advice," Prevention Magazine 52:66 (2000).
Website publication: "A Pure Hawaiian Noni Juice," web.archive.org/web/20030523122956/http://www.nonialoha.com (2003).
Website publication: "Betterman" by Interceuticals, www.naturalhealtheconsultant.com/Monographs/Betterman.html (1998).
Website publication: "*Morinda*," www.drugdigest.org/DD/DV/HebsTake/0,3927,552025/Morinda.00.html (2003).
Website publication: "NONI in the News," www.incc.org/news-june.htm, p. 1-6, (2002).
Website publication: "NONI: Ugly but with a beautiful soul," www.web.archive.org/web/20020207214423/http://wwwInukahivatrading.com/noni.htm (2002).
Website publication: "Noni Juice," www.tipsofallsorts.com/noni.html p. 1-11 (1999).
Website publication "Noni or Nonu Fruit," www.noni-nonu.com (1999).
Website publication "100% Pure Standardized Noni Juice," www.evitamins.com (1999).
Weil, A., "Alternatives," Northern Echo, Darlington, UK, p. 1-2 (2000).
Yamada et al., "Antibacterial Composition" Abstract (1984).
Younos et al., "Analgesic and Behavioural Effects of *Morinda-citrifolia*" Planta Medica 56(5):430-434 (1990).
Bennett et al., "Xanthones from Guttiferae" Phytochemistry vol. 28, No. 4, pp. 967-998 (1989).
Brock et al., "Biology of Microorganisms," 6th Ed. Prentice-Hall, Inc. p. 334 (1994).

(56) References Cited

OTHER PUBLICATIONS

Conquer et al., "Supplementation with quercetin markedly increases plasma quercetin concentration . . . " Journal of Nutrition, vol. 128, Iss. 3, pp. 593-597 (Mar. 1998).

Csiszar et al., "Extracts of *Morinda* . . . Exhibit Selective Anti-Tumor . . . " (Abstract) Proceedings of the American Association for Cancer Research, vol. 42 p. 634 (Mar. 2001).

Cushman et al. "Angiotensin Converting Enzyme Inhibitors: Evolution . . . " Angiotensin Converting Enzyme Inhibitors, Horovitz Ed., pp. 3-25, Urban & Schwarzenberg (1981).

Lee, "MorindaNet plans for e-commerce" New Straits Times, beginning p. 7, (Jun. 17, 1999).

"Angiotensin I-Converting Enzyme; ACE" Online Mendelian Inhereitance in Man, Johns Hopkins University Website Publication, (Mar. 3, 2004).

Singh et al., "Folk Medicine in Tonga: A Study on the Use of Herbal Medicines . . . " Journal of Ethnopharmacology 12 (1984) pp. 305-329.

Wang et al. "Cancer Preventive Effect of *Morinda citrifolia* (Noni)" Annals of the N.Y. Academy of Sciences pp. 161-168 (2001) 952.

Website publication "Tahitian Noni Skin Care Systems," www.nonidrink.com/skin_care.html (2002).

Website publication "Nature's Sunshine Products," wwww.synergeyworldwide.com/SG/products/productlines/products.aspx?product=SG4066 (Feb. 24, 2005).

Bain, J. "Secret World of Noni," Toronto Star, Toronto, Ontario: Aug. 6, 1999, p. 1 (pp. 1-5 of ProQuest).

Navarre, I "76 Ways to Use Noni Fruit Juice for your Better Health" Pride Publishing, Orem, Utah, (Apr. 2001), pp. 57-59, 81-83, and 119-124.

Guardia et al. "Anti-Inflammatory Properties of Plant Flavonoids. Effects of Rutin, Quercetin and Hesperidin on Adjuvant Arthritis in Rat." II Farmaco, 56, (2001) pp. 683-387.

Cimanga et al., Flavonoids O-glycosides from Leaves of *Morinda* Morindoides, Phytochemistry, 1995, 38(5), pp. 1301-1303.

Website Publication, Indo World, Nature'salternative.com, (Jan. 1, 2001), http://www.indo-world.com/profile.htm.

Website Publication, Nature'salternative.com, http://www.naturesalternatives.supplements/noni.html, NutriScience Innovation, http://www.nutriscience.usea.com/productinfo.htm, Mar. 19, 2007 4 pages.

Website Publication, National Cancer Institute, http:/www.cancer.gov,/Templates/drugdictionary.aspx?CdrID=304320 CAT.INST, http://cat.inst.fr/?aModele=afficheNcpsidt=4257124, Mar. 19, 2007 4 pages.

Chye, K.T., "A Juice for Many Ailments," New Straits Times, Aug. 10, 1999, pp. 5 (pp. 1-3 of ProQuest direct).

Sang et al., Analysis of chemical components in noni fruits (*Morinda citrifolia*), PTO-892, abstract. Aug. 2000.

Blanco et al. "The noni fruit (*Morinda citrifolia* L.): A review of agricultural research, nutritional and therapeutic properties," Journal of Food Composition and Analysis, 2006, vol. 19, pp. 645-654.

\* cited by examiner

MORINDA CITRIFOLIA BASED FORMULATIONS FOR REGULATING T CELL IMMUNOMODULATION IN NEONATAL STOCK ANIMALS

RELATED APPLICATIONS

This application claims priority to U.S. Provisional Patent Application No. 60/970,445, filed on Sep. 6, 2007, entitled, "*Morinda Citrifolia* Based Formulations for Regulating T Cell Immunomodulation in Neonatal Stock Animals."

BACKGROUND

1. Field of the Invention

The field of the invention relates to products enhanced with *Morinda citrifolia*, which may be administered to various animals, and more particularly to products for increasing $CD8^+$ T cell activation in animals.

2. Background

A wide variety of different animal food formulations are commercially available. In the past, the nutrients or ingredients in these formulations were not typically designed to provide specific advantages to an animal if desired or needed. Animal food may be specifically designed to decrease the mortality rate of newborn stock animals. For example, the inherent developmental immaturity of the neonatal immune system of various stock animals represents a predisposing factor toward increased morbidity and mortality. Currently, the leading management strategy to diminish this morbidity and mortality, in dairy calves particularly, is through the ingestion of high quality colostrum to ensure adequate passive transfer (APT) of immunoglobulins. While APT is the aim of dairy calf raisers, it may be more easily accomplished on smaller, closed-herd dairies compared to larger, commercial, calf-raising farms.

In addition to immunoglobulins, high quality colostrum includes a full compliment of cytokines, growth factors, hormones and maternal leukocytes which play a central role in modulating neonatal, innate and adaptive immunity. Bovine colostrum is known to contain several cytokines, such as: IFN-γ, IL-1β, IL-1ra, IL-4, IL-6, IL-18, and TNF-α. Many of which can be found in their highest concentrations immediately after parturition, followed by a rapid decline in milk by five days postpartum. Various studies show that orally administered leukocytes and cytokines are readily absorbed and enter the circulation of the neonate.

Adaptive immunity requires a full repertoire of functional T cells, including $CD4^+$ T helper cells, cytotoxic $CD8^+$ T cells CTL, and γδ $TCR^+$ subsets, in the defense against infections such as bovine herpesvirus-1 (BHV-1), bovine viral diarrhea virus (BVDV) and bovine respiratory syncytial virus (BRSV).

T helper cells express $CD4^+$ and are composed of two major populations, T helper 1 (Th1) and T helper 2 (Th2) cells. These T cell subsets play an important role in coordinating the overall adaptive immune response by modulating the activities of many immune cells like macrophage-activation through secretion of cytokines such as IL-2 and IFN-γ. Effector $CD4^+$ T cells help B cell responses and enhance $CD8^+$ T cell development through activation of APC or secretion of cytokines, such as IL-2, IL-4, and IL-5. It is also well established that neonatal immunity favors a Th2 respond in the face of an invading pathogen. This bias against a Th1 response, during which pro-inflammatory cytokines are produced, reduces the possibility of alloimmune reactions between mother and fetus and helps protect against infection both in and ex utero. However, this Th2 biased cell response contributes to reduced vaccine responses and leaves the neonate more susceptible to microbial infection. Repeated antigen exposure over time, diminishing the Th2 cell polarization and/or increasing the Th1 cell polarization, accelerates the immune maturing process and potentially reduces allergy and atopy. The Th1 immune response, which can be detrimental during pregnancy, becomes increasingly important postpartum as it leads to the production of $CD8^+$ CTL. These cells play a crucial role in the immune system with the ability to lyse infected cells.

γδ T-cells make up the smallest fraction of lymphocytes in the ileal mucosa and the largest fraction of PBMC in young calves. They have a wide range of functions, yet their role in immune surveillance and pathogen recognition is still poorly understood. There is evidence that γδ T cell function includes cytokine production and cytotoxic activity as well as immunomodulation and inflammatory response. Bovine γδ T-cells found in the spleen are more transcriptionally active than those located in the blood, which represent only a small fraction of circulating T lymphocytes.

The second leading management strategy in preventing neonatal losses is through the administration of antibiotics in milk replacer or by injection as a therapeutic use and/or prophylactic strategy. While this strategy is associated with reduced calf morbidity and mortality, this management technique is highly scrutinized for possibly speeding the development of antibiotic resistant pathogens and resulting in an un-organic product for consumers. In fact, as of 2003 the European Union had already banned the use of antibiotics and related drugs on livestock for the purpose of growth promotion. These restrictions are intended to preserve antibiotic effectiveness for human use. The World Health Organization has also recommended the cessation of use of growth-promoting antibiotics in production anaimals, and some anticipate that the United States will adopt similar restrictions in the near future.

As a result of consumer pressure, there has been a push for safe, natural, sustainable immunomodulators to enhance calf health and lower morbidity and mortality rates. Dietary supplements that can reduce industry dependency on antibiotics while increasing the likelihood of successful APT and improving immune function are being sought after. A wide range of immunomodulators including peptides, lipopolysaccharides, glycoproteins, lipid derivatives, proteins and substances isolated from microorganisms, have been identified and tested with varying degrees of success in the clinical setting.

Immunomodulators from botanical sources have received much notoriety for their immune enhancing effects, relatively low toxicity and bio-availability. One type of immunomodulator, polyunsaturated fatty acids, have been used to increase the energy density of animal diets and provide immune modulation. Optimal amounts of vitamins A and E have been shown to prompt immune responses similar to that of adult cattle. Calves from dams supplemented with mannan oligosaccharide tended to have greater serum rotavirus neutralizing titers and serum protein concentrations compared to control calves.

*Morinda citrifolia* (noni) fruit is a well recognized natural herbal product that reportedly has a broad range of antibacterial, anti-inflammatory, immune stimulatory and anti-tumor effects. The juice from the *Morinda citrifolia* fruit is considered to have an immune stimulatory effect mediated by a polysaccharide-rich substance, noni-precipitant (ppt).

Because most of the common medical treatments for the numerous medical problems discussed above can involve serious side effects, compositions containing natural products and nutraceuticals that would treat these diseases and syndromes with less contraindications and diminish the development of antibiotic resistance are highly desirable, not only to relieve suffering in the animals but also to improve the quality of human health.

SUMMARY OF THE INVENTION

The present invention is directed to various formulas and methods of administering various *Morinda citrifolia* enhanced immunomodulators to animals to enhance animal health and lower morbidity and mortality rates. Therefore, preferred embodiments of the present invention provide a *M. citrifolia* enhanced product, which may be administered to animals.

Some embodiments of the invention include one or more processed *Morinda citrifolia* components such as: extract from the leaves of *Morinda citrifolia*, leaf hot water extract, processed *Morinda citrifolia* leaf ethanol extract, processed *Morinda citrifolia* leaf steam distillation extract, *Morinda citrifolia* fruit juice, *Morinda citrifolia* extract, *Morinda citrifolia* dietary fiber, *Morinda citrifolia* puree juice, *Morinda citrifolia* puree, *Morinda citrifolia* fruit juice concentrate, *Morinda citrifolia* puree juice concentrate, freeze concentrated *Morinda citrifolia* fruit juice, and evaporated concentration of *Morinda citrifolia* fruit juice, whole *Morinda citrifolia* fruit in fresh, whole dried *Morinda citrifolia* fruit, powder or solvent extracted forms as well as enzyme treated *Morinda citrifolia* seeds, or any other processed *Morinda citrifolia* seed (i.e. roasting, blanching, microwaving, heat treatment, soaking in water or water solutions of various salts or chemical compounds), whole *Morinda citrifolia* fruit with blossoms or flowers attached, leaf extracts, leaf juice, and defatted and untreated seed extracts.

Preferred embodiments of the present invention provide delivery systems, methods, and apparatus for providing to animals food products containing *Morinda citrifolia* puree and other additives such as seed extracts, fatty acids and minerals. Examples of these delivery systems include pellets, extruded nuggets, extruded flakes, sinking nuggets, delivery in liquid form via a water system or lick tank system, semisolid and gelatinous forms, low moisture gels, low moisture gel pellets, crumble, mash, loose feed, sweet feed, and liquid drenching. The present invention contemplates administering these various forms of *Morinda citrifolia* enhanced products by either integrating the products into the feed typically provided for the animal, or as a top dressing. Other administration methods include colostrums administered to newborn calves soon after birth.

DETAILED DESCRIPTION OF THE PREFERRED EMBODIMENTS

The present invention contemplates administering various forms of *M. citrifolia* with and without additional nutrients. Non-limiting examples of products which may be administered to animals include: *M. citrifolia* plus glycosaminoglycans, *M. citrifolia* plus hyaluronic acid, *M. citrifolia* plus glucosamine HCl, *M. citrifolia* plus glucosamine sulfate, and *M. citrifolia* plus chondroitin sulfate. Other non limiting examples of formulations containing *M. citrifolia* which may be administered to animals include: *M. citrifolia* plus essential amino acids, *M. citrifolia* plus essential fatty acids, *M. citrifolia* plus long chain fatty acids, *M. citrifolia* plus omega 3 fatty acids, *M. citrifolia* plus omega 6 fatty acids, *M. citrifolia* plus macro minerals, *M. citrifolia* plus micro minerals, *M. citrifolia* plus peptides chains, *M. citrifolia* plus branched chain amino acids, *M. citrifolia* puree plus whole noni seeds, *M. citrifolia* puree plus whole roasted noni seeds, *M. citrifolia* puree plus whole roasted defatted noni seeds, *M. citrifolia* puree plus roasted cracked noni seeds defatted, *M. citrifolia* puree plus roasted cracked noni seeds, *M. citrifolia* puree plus roasted ground noni seeds, *M. citrifolia* puree plus roasted ground noni seeds defatted, *M. citrifolia* puree plus roasted flaked noni defatted seeds, *M. citrifolia* puree plus roasted flaked noni seeds, *M. citrifolia* puree plus roasted extruded noni defatted seeds, and *M. citrifolia* puree plus roasted extruded noni seeds and seed extracts.

The present invention contemplates administration of various forms of *M. citrifolia* with and without additional nutrients in order to enhance the development of immune systems of various stock animals. Developmental immaturity of the immune system renders stock animals vulnerable to high rates of morbidity and mortality. Ingesting colostrum containing maternal immunoglobulins, leukocytes and cytokines are the animals' best defense in ensuring its health and survival. Preferred embodiments of the present invention are designed to positively affect the immune systems of feeding neonatal calves, including administration of noni puree to effect bacterial killing, lymphocyte proliferation and CD25 expression on $CD4^+$, $CD8^+$ and $\gamma\delta$ T cells.

General Description of the *Morinda citrifolia* L. Plant

The Indian Mulberry or *Morinda citrifolia* plant, known scientifically as *Morinda citrifolia* L. ("*Morinda citrifolia*"), is a shrub or small tree. The plant is native to Southeast Asia and has spread in early times to a vast area from India to eastern Polynesia. It grows randomly in the wild, and it has been cultivated in plantations and small individual growing plots. When fully ripe, the fruit has a pronounced odor like rancid cheese. Although the fruit has been eaten by several nationalities as food, the most common use of the *Morinda citrifolia* plant has traditionally been as a red and yellow dye source.

1. Processing *Morinda Citrifolia* Leaves

The leaves of the *Morinda citrifolia* plant are one possible component of the *Morinda citrifolia* plant that may be present in some compositions of the present invention. For example, some compositions comprise leaf extract and/or leaf juice as described further herein. Some compositions comprise a leaf serum that is comprised of both leaf extract and fruit juice obtained from the *Morinda citrifolia* plant. Some compositions of the present invention comprise leaf serum and/or various leaf extracts as incorporated into a nutraceutical product ("nutraceutical" herein referring to any drug or product designed to improve the health of living organisms such as human beings or other animals).

In some embodiments of the present invention, the *Morinda citrifolia* leaf extracts are obtained using the following process. First, relatively dry leaves from the *Morinda citrifolia* L. plant are collected, cut into small pieces, and placed into a crushing device—preferably a hydraulic press—where the leaf pieces are crushed. In some embodiments, the crushed leaf pieces are then percolated with an alcohol such as ethanol, methanol, ethyl acetate, or other alcohol-based derivatives using methods known in the art. Next, in some embodiments, the alcohol and all alcohol-soluble ingredients are extracted from the crushed leaf pieces, leaving a leaf extract that is then reduced with heat to remove all the liquid therefrom. The resulting dry leaf extract will herein be referred to as the "primary leaf extract."

In some embodiments of the present invention, the primary leaf extract is pasteurized to at least partially sterilize the extract and destroy objectionable organisms. The primary leaf extract is pasteurized preferably at a temperature ranging from 70 to 80 degrees Celsius and for a period of time sufficient to destroy any objectionable organisms without major chemical alteration of the extract. Pasteurization may also be accomplished according to various radiation techniques or methods.

In some embodiments of the present invention, the pasteurized primary leaf extract is placed into a centrifuge decanter where it is centrifuged to remove or separate any remaining leaf juice therein from other materials, including chlorophyll. Once the centrifuge cycle is completed, the leaf extract is in a relatively purified state. This purified leaf extract is then pasteurized again in a similar manner as discussed above to obtain a purified primary leaf extract.

Preferably, the primary leaf extract, whether pasteurized and/or purified, is further fractionated into two individual fractions: a dry hexane fraction, and an aqueous methanol fraction. This is accomplished preferably via a gas chromatograph containing silicon dioxide and $CH_2Cl_2$-MeOH ingredients using methods well known in the art. In some embodiments of the present invention, the methanol fraction is further fractionated to obtain secondary methanol fractions. In some embodiments, the hexane fraction is further fractionated to obtain secondary hexane fractions.

One or more of the leaf extracts, including the primary leaf extract, the hexane fraction, methanol fraction, or any of the secondary hexane or methanol fractions may be combined with the fruit juice of the fruit of the *Morinda citrifolia* plant to obtain a leaf serum (the process of obtaining the fruit juice to be described further herein). In some embodiments, the leaf serum is packaged and frozen ready for shipment; in others, it is further incorporated into a nutraceutical product as explained herein.

2. Processing *Morinda Citrifolia* Fruit

Some embodiments of the present invention include a composition comprising fruit juice of the *Morinda citrifolia* plant. In some embodiments, processed *Morinda citrifolia* fruit juice can be prepared by separating seeds and peels from the juice and pulp of a ripened *Morinda citrifolia* fruit; filtering the pulp from the juice; and packaging the juice. Alternatively, rather than packaging the juice, the juice can be immediately included as an ingredient in another product, frozen or pasteurized. In some embodiments of the present invention, the juice and pulp can be pureed into a homogenous blend to be mixed with other ingredients. Other processes include freeze drying the fruit and juice. The fruit and juice can be reconstituted during production of the final juice product. Still other processes may include air drying the fruit and juices prior to being masticated.

In a currently preferred process of producing *Morinda citrifolia* fruit juice, the fruit is either hand picked or picked by mechanical equipment. The fruit can be harvested when it is at least one inch (2-3 cm) and up to 12 inches (24-36 cm) in diameter. The fruit preferably has a color ranging from a dark green through a yellow-green up to a white color, and gradations of color in between. The fruit is thoroughly cleaned after harvesting and before any processing occurs.

The fruit is allowed to ripen or age from 0 to 14 days, but preferably for 2 to 3 days. The fruit is ripened or aged by being placed on equipment so that the fruit does not contact the ground. The fruit is preferably covered with a cloth or netting material during aging, but the fruit can be aged without being covered. When ready for further processing the fruit is light in color, such as a light green, light yellow, white or translucent color. The fruit is inspected for spoilage or for excessive green color and firmness. Spoiled and hard green fruit is separated from the acceptable fruit.

The ripened and aged fruit is preferably placed in plastic lined containers for further processing and transport. The containers of aged fruit can be held from 0 to 30 days, but preferably the fruit containers are held for 7 to 14 days before processing. The containers can optionally be stored under refrigerated conditions prior to further processing. The fruit is unpacked from the storage containers and is processed through a manual or mechanical separator. The seeds and peel are separated from the juice and pulp.

The juice and pulp can be packaged into containers for storage and transport. Alternatively, the juice and pulp can be immediately processed into a finished juice product. The containers can be stored in refrigerated, frozen, or room temperature conditions. The *Morinda citrifolia* juice and pulp are preferably blended in a homogenous blend, after which they may be mixed with other ingredients, such as flavorings, sweeteners, nutritional ingredients, botanicals, and colorings. The finished juice product is preferably heated and pasteurized at a minimum temperature of 83° C. or higher up to 100° C. Another product manufactured is *Morinda citrifolia* puree and puree juice, in either concentrate or diluted form. Puree is essentially the pulp separated from the seeds and is different than the fruit juice product described herein.

The product may be filled and sealed into a final container of plastic, glass, or another suitable material that can withstand the processing temperatures. The containers may be maintained at the filling temperature or may be cooled rapidly and then placed in a shipping container. The shipping containers are preferably wrapped with a material and in a manner to maintain or control the temperature of the product in the final containers.

The juice and pulp may be further processed by separating the pulp from the juice through filtering equipment. The filtering equipment preferably consists of, but is not limited to, a centrifuge decanter, a screen filter with a size from 1 micron up to 2000 microns, more preferably less than 500 microns, a filter press, a reverse osmosis filtration device, and any other standard commercial filtration devices. The operating filter pressure preferably ranges from 0.1 psig up to about 1000 psig. The flow rate preferably ranges from 0.1 g.p.m. up to 1000 g.p.m., and more preferably between 5 and 50 g.p.m. The wet pulp is washed and filtered at least once and up to 10 times to remove any juice from the pulp. The resulting pulp extract typically has a fiber content of 10 to 40 percent by weight. The resulting pulp extract is preferably pasteurized at a temperature of 83° C. minimum and then packed in drums for further processing or made into a high fiber product.

3. Processing *Morinda Citrifolia* Seeds

Some *Morinda citrifolia* compositions of the present invention include seeds from the *Morinda citrifolia* plant. In some embodiments of the present invention, *Morinda citrifolia* seeds are processed by pulverizing them into a seed powder in a laboratory mill. In some embodiments, the seed powder is left untreated. In some embodiments, the seed powder is further defatted by soaking and stirring the powder in hexane—preferably for 1 hour at room temperature (Drug: Hexane—Ratio 1:10). The residue, in some embodiments, is then filtered under vacuum, defatted again (preferably for 30 minutes under the same conditions), and filtered under vacuum again. The powder may be kept overnight in a fume hood in order to remove the residual hexane.

Still further, in some embodiments of the present invention, the defatted and/or untreated powder is extracted, preferably with ethanol 50% (m/m) for 24 hours at room temperature at a drug solvent ratio of 1:2.

4. Processing Morinda Citrifolia Oil

Some embodiments of the present invention may comprise oil extracted from the *Morinda citrifolia* plant. The method for extracting and processing the oil is described in U.S. patent application Ser. No. 09/384,785, filed on Aug. 27, 1999 and issued as U.S. Pat. No. 6,214,351 on Apr. 10, 2001, which is incorporated by reference herein. The *Morinda citrifolia* oil typically includes a mixture of several different fatty acids as triglycerides, such as palmitic, stearic, oleic, and linoleic fatty acids, and other fatty acids present in lesser quantities. In addition, the oil preferably includes an antioxidant to inhibit spoilage of the oil. Conventional food grade antioxidants are preferably used.

5. Compositions and Their Use

Animal food products have become more advanced in their ability to specifically target and cater to specific needs of different animals. Several animal food preparations are disclosed in U.S. Pat. No. 6,737,089 which is incorporated herein in its entirety.

The present invention features compositions and methods for administering various *M. citrifolia* enhanced products to animals to improve various physiological conditions. For example the products of the present invention may be utilized to enhance immunity. Embodiments of the resent invention also comprise methods for internally and/or externally introducing a *Morinda citrifolia* composition to the body of an animal. Several embodiments of the *Morinda citrifolia* compositions comprise various different ingredients, each embodiment comprising one or more forms of a processed *Morinda citrifolia* component as taught and explained herein.

Some embodiments of the invention include one or more processed *Morinda citrifolia* components such as: extract from the leaves of *Morinda citrifolia*, leaf hot water extract, processed *Morinda citrifolia* leaf ethanol extract, processed *Morinda citrifolia* leaf steam distillation extract, *Morinda citrifolia* fruit juice, *Morinda citrifolia* extract, *Morinda citrifolia* dietary fiber, *Morinda citrifolia* puree juice, *Morinda citrifolia* puree, *Morinda citrifolia* fruit juice concentrate, *Morinda citrifolia* puree juice concentrate, freeze concentrated *Morinda citrifolia* fruit juice, and evaporated concentration of *Morinda citrifolia* fruit juice, whole *Morinda citrifolia* fruit in fresh, whole dried *Morinda citrifolia* fruit, powder or solvent extracted forms as well as enzyme treated *Morinda citrifolia* seeds, or any other processed *Morinda citrifolia* seed (i.e. roasting, blanching, microwaving, heat treatment, soaking in water or water solutions of various salts or chemical compounds), whole *Morinda citrifolia* fruit with blossoms or flowers attached, leaf extracts, leaf juice, and defatted and untreated seed extracts. Compositions of the present invention may also include various other ingredients. Examples of other ingredients include, but are not limited to: artificial flavoring, other natural juices or juice concentrates such as a natural grape juice concentrate or a natural blueberry juice concentrate; carrier ingredients; and others as will be further explained herein.

Any compositions having the leaf extract from the *Morinda citrifolia* leaves, may comprise one or more of the following: the primary leaf extract, the hexane fraction, methanol fraction, the secondary hexane and methanol fractions, the leaf serum, or the nutraceutical leaf product.

In some embodiments of the present invention, active ingredients or compounds of *Morinda citrifolia* components may be extracted out using various procedures and processes commonly known in the art. For instance, the active ingredients may be isolated and extracted using alcohol or alcohol-based solutions, such as methanol, ethanol, and ethyl acetate, and other alcohol-based derivatives using methods known in the art. These active ingredients or compounds may be isolated and further fractioned or separated from one another into their constituent parts. Preferably, the compounds are separated or fractioned to identify and isolate any active ingredients that might help to prevent disease, enhance health, or perform other similar functions. In addition, the compounds may be fractioned or separated into their constituent parts to identify and isolate any critical or dependent interactions that might provide the same health-benefiting functions just mentioned.

The present invention contemplates administering various forms of *M. citrifolia* with additional nutrients. Non-limiting examples of products which may be administered to animals include: *M. citrifolia* plus glycosaminoglycans, *M. citrifolia* plus hyaluronic acid, *M. citrifolia* plus glucosamine HCl, *M. citrifolia* plus glucosamine sulfate, and *M. citrifolia* plus chondroitin sulfate. Other non limiting examples of formulations containing *M. citrifolia* which may be administered to animals include: *M. citrifolia* plus essential amino acids, *M. citrifolia* plus essential fatty acids, *M. citrifolia* plus long chain fatty acids, *M citrifolia* plus omega 3 fatty acids, *M. citrifolia* plus omega 6 fatty acids, *M. citrifolia* plus macro minerals, *M. citrifolia* plus micro minerals, *M. citrifolia* plus peptides chains, *M. citrifolia* plus branched chain amino acids, *M. citrifolia* puree plus whole noni seeds, *M. citrifolia* puree plus whole roasted noni seeds, *M. citrifolia* puree plus whole roasted defatted noni seeds, *M. citrifolia* puree plus roasted cracked noni seeds defatted, *M. citrifolia* puree plus roasted cracked noni seeds, *M. citrifolia* puree plus roasted ground noni seeds, *M. citrifolia* puree plus roasted ground noni seeds defatted, *M. citrifolia* puree plus roasted flaked noni defatted seeds, *M. citrifolia* puree plus roasted flaked noni seeds, *M. citrifolia* puree plus roasted extruded noni defatted seeds, and *M. citrifolia* puree plus roasted extruded noni seeds.

The present invention contemplates administering various forms of *M. citrifolia* enhanced products. Non-limiting examples of those forms include: pellet, extruded nugget, extruded flake, sinking nugget, liquid via water system, liquid via lick-tank system, semi-solid, gel, low moisture gel, and low moisture gel pellet.

Method of delivery of the *M. citrifolia* enhanced products may be very important. Some non-limiting examples of methods of delivery include top dressing feed with a *M. citrifolia* product, adding it to the feeding practices used for new calves including adding *M. citrifolia* product to the colostrums administered to new born calves soon after birth, dipping with *M. citrifolia* enhanced products to ameliorate mastitis in the dairy industry.

There are several considerations that may be included in the assessment of what form of administration the *M. citrifolia* product should take. Some non-limiting examples of consideration include: palatability; will the cows/animals eat the product, suggested intake; what will be the proper dosage, milk flavor; will it taint the flavor of the milk in the dairy industry, incorporation into the feed; can it conveniently be added to the feed without significantly reducing its effectiveness, and uniformity of mixing; and can it be mixed into the feed in a uniform and consistent way so that we can be sure that each animal is getting the proper dosage.

In preferred embodiments, the *M. citrifolia* enhanced products are thoroughly mixed with the food consumed by the animals. In a non-limiting example we propose mixing the *M. citrifolia* enhanced products with grains, hay, milk or milk substitute. In another non-limiting example we propose missing the *M. citrifolia* with a liquid medicator (e.g. wherein the liquid is water).

Any components and compositions of *Morinda citrifolia* may be further incorporated into a nutraceutical product (again, "nutraceutical" herein referring to any product designed to improve the health of living organisms such as humans and/or other animals). Examples of nutraceutical products may include, but are not limited to: intravenous products, topical dermal products, first-aid products, antibacterial products, immune system enhancing products, anti-inflammatory products, eye drops, antifungal products, and various nutraceutical and other products as may be further discussed herein.

The compositions of the present invention may be formulated into any of a variety of embodiments, including oral compositions, topical dermal solutions, intravenous solutions, and other products or compositions.

Oral compositions may take the form of, for example, tablets, boluses, lozenges, aqueous or oily suspensions, dispersible powders or granules, emulsions, syrups, or elixirs. Compositions intended for oral use may be prepared according to any method known in the art, and such compositions may contain one or more agents such as sweetening agents, flavoring agents, coloring agents, and preserving agents. They may also contain one or more additional ingredients such as vitamins and minerals, etc. Tablets may be manufactured to contain one or more *Morinda citrifolia* components in admixture with non-toxic, pharmaceutically acceptable excipients that are suitable for the manufacture of tablets. These excipients may be, for example, inert diluents, granulating and disintegrating agents, binding agents, and lubricating agents. The tablets may be uncoated or they may be coated by known techniques to delay disintegration and absorption in the gastrointestinal tract and thereby provide sustained action over a longer period. For example, a time delay material such as glyceryl monostearate or glyceryl distearate may be used.

Aqueous suspensions may be manufactured to contain the *Morinda citrifolia* components in admixture with excipients suitable for the manufacture of aqueous suspensions. Examples of such excipients include, but are not limited to: suspending agents such as sodium carboxymethyl-cellulose, methylcellulose, hydroxy-propylmethycellulose, sodium alginate, polyvinyl-pyrrolidone, gum tragacanth and gum acacia; dispersing or wetting agents such as a naturally-occurring phosphatide like lecithin, or condensation products of an alkylene oxide with fatty acids such as polyoxyethylene stearate, or condensation products of ethylene oxide with long chain aliphatic alcohols such as heptadecaethylene-oxycetanol, or condensation products of ethylene oxide with partial esters derived from fatty acids and a hexitol such as polyoxyethylene sorbitor monooleate, or condensation products of ethylene oxide with partial esters derived from fatty acids and hexitol anhydrides such as polyethylene sorbitan monooleate.

Typical sweetening agents may include, but are not limited to: natural sugars derived from corn, sugar beets, sugar cane, potatoes, tapioca, or other starch-containing sources that can be chemically or enzymatically converted to crystalline chunks, powders, and/or syrups. Also, sweeteners can comprise artificial or high-intensity sweeteners, some of which may include aspartame, sucralose, stevia, saccharin, etc. The concentration of sweeteners may be between from 0 to 50 percent by weight of the *Morinda citrifolia* composition, and more preferably between about 1 and 5 percent by weight.

Typical flavoring agents can include, but are not limited to, artificial and/or natural flavoring ingredients that contribute to palatability. The concentration of flavors may range, for example, from 0 to 15 percent by weight of the *Morinda citrifolia* composition. Coloring agents may include food-grade artificial or natural coloring agents having a concentration ranging from 0 to 10 percent by weight of the *Morinda citrifolia* composition.

Typical nutritional ingredients may include vitamins, minerals, trace elements, herbs, botanical extracts, bioactive chemicals, and compounds at concentrations from 0 to 10 percent by weight of the *Morinda citrifolia* composition. Examples of vitamins include, but are not limited to, vitamins A, B1 through B12, C, D, E, Folic Acid, Pantothenic Acid, Biotin, etc. Examples of minerals and trace elements include, but are not limited to, calcium, chromium, copper, cobalt, boron, magnesium, iron, selenium, manganese, molybdenum, potassium, iodine, zinc, phosphorus, etc. Herbs and botanical extracts may include, but are not limited to, alfalfa grass, bee pollen, chlorella powder, Dong Quai powder, Ecchinacea root, *Gingko Biloba* extract, Horsetail herb, Indian mulberry, Shitake mushroom, spirulina seaweed, grape seed extract, etc. Typical bioactive chemicals may include, but are not limited to, caffeine, ephedrine, L-carnitine, creatine, lycopene, etc.

The ingredients to be utilized in a topical dermal product may include any that are safe for internalizing into the body of a mammal and may exist in various forms, such as gels, lotions, creams, ointments, etc., each comprising one or more carrier agents. The ingredients or carrier agents incorporated into systemically (e.g., intravenously) administered compositions may also comprise any known in the art.

In one exemplary embodiment, a *Morinda citrifolia* composition of the present invention comprises one or more of a processed *Morinda citrifolia* component present in an amount by weight between about 0.01 and 100 percent by weight, and preferably between 0.01 and 95 percent by weight. Several embodiments of formulations are included in U.S. Pat. No. 6,214,351, issued on Apr. 10, 2001, which is incorporated in its entirety herein. However, these compositions are only intended to be exemplary, as one ordinarily skilled in the art will recognize other formulations or compositions comprising the processed *Morinda citrifolia* product.

In another exemplary embodiment, the internal composition comprises the ingredients of: processed *Morinda citrifolia* fruit juice or puree juice present in an amount by weight between about 0.1-80 percent; processed *Morinda citrifolia* oil present in an amount by weight between about 0.1-20 percent; and a carrier medium present in an amount by weight between about 20-90 percent. *Morinda citrifolia* puree juice or fruit juice may also be formulated with a processed *Morinda citrifolia* dietary fiber product present in similar concentrations.

The juice and pulp can be dried using a variety of methods. The juice and pulp mixture can be pasteurized or enzymatically treated prior to drying. The enzymatic process begins with heating the product to a temperature between 32.9° C. and 57.2° C. It is then treated with either a single enzyme or a combination of enzymes. These enzymes include, but are not limited to, amylase, lipase, protease, cellulase, bromelin, etc. The juice and pulp can also be dried with other ingredients, such as those described above in connection with the high fiber product. The typical nutritional profile of the dried juice and pulp is 1 to 20 percent moisture, 0.1 to 15 percent protein, 0.1 to 20 percent fiber, and the vitamin and mineral content.

The filtered juice and the water from washing the wet pulp are preferably mixed together. The filtered juice is preferably vacuum evaporated to a brix of 40 to 70 and a moisture of 0.1 to 80 percent, more preferably from 25 to 75 percent. The resulting concentrated *Morinda citrifolia* juice may or may not be pasteurized. The juice would not be pasteurized in circumstances where the sugar content or water activity was sufficiently low enough to prevent microbial growth. It is packaged for storage, transport and/or further processing.

Animal food products have become more advanced in their ability to specifically target and cater to specific needs of different animals. Several animal food preparations are disclosed in U.S. Pat. No. 6,737,089 which is incorporated herein in its entirety.

6. Delivery Forms and Systems

The present invention contemplates administering various forms of *M. citrifolia* enhanced products. Non-limiting examples of those forms include: pellet, extruded nugget, extruded flake, sinking nugget, liquid via water system, liquid via lick-tank system, semi-solid, gel, low moisture gel, and low moisture gel pellet.

Methods of Delivery

Some non-limiting examples of methods of delivery include top dressing feed with a *M. citrifolia* product, adding it in liquid form to the dry feed normally given that species or drying the *M. citrifolia* product and adding it in ground, granular or pellet form. Liquid *M. citrifolia* products are simply mixed in the proper ratio with other liquid feed. Sinking pellets are used for fish or other water dwelling creatures. The *M. citrifolia* additives whether liquid or dry are mixed into the feed in a uniform and consistent way so that it can be assured that each animal is getting the proper amount for uniform benefits.

One method for administering the *M. citrifolia* enhanced food products is by administering a large liquid dose or "drenching" ("drenching") means giving each cow, horse, sheep and/or other animal about a quart or a liter of product at once down the throat of *M. citrifolia* enhanced products.

Forms of Administration

The present invention contemplates administering various forms of *M. citrifolia* enhanced products. Non-limiting examples of those forms include: pellet, extruded nugget, extruded flake, sinking nugget, liquid via water system, liquid via lick-tank system, semi-solid, gel, low moisture gel, low moisture gel pellet.

Method of delivery of the *M. citrifolia* enhanced products may be very important. Some non-limiting examples of methods of delivery include top dressing feed with a *M. citrifolia* product, adding it to the feeding practices used for new calves including adding *M. citrifolia* product to the colostrums administered to new born calves soon after birth.

Decreasing the use of antibiotics may be achieved by administering various *M. citrifolia* enhanced products in their place.

7. Examples

The following examples are given to illustrate various embodiments which have been made or may be made in accordance with the present invention and are given by way of example only. It is to be understood that the following examples are not all inclusive, comprehensive, or exhaustive of the many types of embodiments of the present invention which can be prepared in accordance with the technology as described herein.

Example 1

Calf Trials

Developmental immaturity of the immune system renders neonatal calves vulnerable to high rates of morbidity and mortality. Ingesting colostrum containing maternal immunoglobulins, leukocytes and cytokines is the calf's best defense in ensuring its health and survival. The objective of this study was to evaluate the immune modulating effects of feeding neonatal calves noni puree by measuring bacterial killing, lymphocyte proliferation and CD25 expression on $CD4^+$, $CD8^+$ and $\gamma\delta$ T cells. Eighteen newborn Holstein bull calves were acquired in pairs from local dairies. All calves had received 4.0 L of pooled colostrum by 12 h of age and were confirmed to have adequate passive transfer (APT) at 24 h of age. The calves were divided into two groups. Group 1 comprised of control calves, while Group 2 received 30 ml (1 oz). of noni puree twice daily in milk replacer. Day 0 samples were obtained between 36 and 48 h of age and before the first feeding of puree. Blood samples were collected from each calf on days 0, 3, 7, and 14. A bactericidal assay was performed to estimate percent killing of *Esherichia coli* and *Staphylococcus epidermidis*. To measure lymphocyte proliferation, a mitogen induced Lymphocyte Blastogenesis Test (LBT) was performed. Mitogen induced activation of $CD4^+$, $CD8^+$ and $\gamma\delta$ T cells was also evaluated by the up-regulation of the IL-2 receptor, CD25, on these cells with two-color flow cytometry. Concanavalin A (ConA) and phytohemagglutinin (PHA) were used as global mitogens. Results showed noni puree-fed calves had a significant increase in CD25 percent expression on $CD8^+$ T cells on day 3 of the study or approximately 5 days postpartum. CD25 percent expression on $CD4^+$ T cells was also higher in noni puree fed calves on day 3 but not in a statistically significant way. Both findings were in response to ConA stimulation. LBTs did not show significant differences between the two groups in response to either mitogen.

Materials and Methods

Acid citrate dextrose-A (ACD-A) was prepared with 2.2 g sodium citrate (dehydrate), 0.8 g citric acid (monohydrate), 2.5 g dextrose and 100 ml $H_2O$ q.s. A cell lysing solution of pH 7.2 was prepared by dissolving 1.5 g (10.6 mM) $Na_2HPO_4$ and 0.32 g (2.7 mM) $NaH_2PO_4$ in 1 L $H_2O$ q.s. A restoring solution of pH 7.2 was similarly prepared by dissolving 1.5 g (10.6 mM) $Na_2HPO_4$, 0.32 g (2.7 mM) $NaH_2PO_4$ and 27 g (462.0 mM) NaCl in 1 L $H_2O$ q.s.

Animals for this project were obtained from six local dairies. Eighteen newborn Holstein bull calves having received 4.0 L of pooled colostrum by 12 h of age arrived in pairs at the Veterinary Medical Teaching Hospital within 12 h of birth where they were housed in individual pens. Within each calf pair, the animals were randomly unloaded from the trailer by hospital personnel and assigned to treatment groups and housing in the order they were removed from the calf trailer. No further randomization was attempted.

Upon arrival, every animal received a physical examination, followed by daily examinations, including temperature, ease of cough induction, fecal consistency, and presence and severity of ocular or otic abnormalities. Calf health evaluations, which were recorded as calf health scores (Table 1), were overseen by veterinarians blinded to treatment groups. Any calf receiving a total health score of five or more for three consecutive days was removed from the study and treated appropriately. APT (IgG>1000 mg/dl) was confirmed for all calves with the IgG Midland Quick Test Kite® at 24 h of age.

Calf pairs consisted of one noni puree fed and one control calf. Calves were bottle fed 2 L of non-medicated milk replacer (CALF GLO®, Vita Plus Corporation, Madison, Wis.) reconstituted according to manufacturer's label twice daily for the first seven days, and 2.5 L twice daily from day 8 to 14. Noni puree fed calves received 30 ml of noni puree twice a day in milk replacer. Calves had access to 125 g calf starter and 4 L of fresh water per day. Of the eight calf pairs, only three pairs had differing health scores between calves on day 0; in two pairs the score was one unit higher for the control calf, and in one pair it was one unit higher for the noni-fed calf. No calves were removed from the study due to health reasons.

Twenty five ml of ACD-A anti-coagulated blood was collected in vacutainer tubes (Becton Dickinson, Franklin Lakes, N.J.) from the jugular vein from each calf on days 0, 3, 7, and 14. Samples were obtained from each calf between 36 and 48 h of age before the first feeding of noni puree which constituted day 0 of the study.

The blood was diluted 1:1 with PBS for the flow cytometry and LBT assays. The buffy coat was harvested following centrifugation at 920×g for 30 min at 25° C., diluted with plasma, layered over 1.083 Ficoll-Histopaque (Sigma, St. Louis, Mo.) and centrifuged at 1380×g for 30 min at 25° C. The PBMC interphase layer was harvested and the remaining red blood cells were exposed to a lysing solution for 1 min, which was neutralized with a restoring solution. The PBMC were washed twice, once with PBS, once with RPMI 1640, at 280×g for 10 min and subsequently resuspended in RPMI 1640 (Mediatech, Inc., Herndon, Va.) with 20% FCS. Cells were stained with Trypan blue to confirm cell viability (>95%) and adjusted with RPMI 1640 with 20% FCS to $5 \times 10^6$ cells/ml.

For flow cytometry analysis, 50 µl of PBMC ($5 \times 10^6$ cells/ml) were cultured on a Costar flat bottom tissue culture treated 96 well plate (Corning, Inc., Corning, N.Y.). Unstimulated control wells contained 100 µl RPMI 1640+20% FCS. Stimulated sample wells contained 100 µl of ConA (final concentration of 6.7 µg/ml; Sigma, St. Louis, Mo.) or 100 µl of the M form of PHA (Gibco, Invitrogen Corp., Carlsbad, Calif.) diluted 1:200 in RPMI 1640. Plates were incubated for 72 h at 37° C. at 5% $CO_2$.

After incubation, the cells were transferred into 12×75 mm polystyrene round bottom tubes (Becton Dickinson, Franklin Lakes, N.J.) and washed with PBS at 520×g for 7 min at 25° C. The cells were resuspended and stained for two-color flow cytometry with the primary antibodies (15 µg/ml; VMRD, Pullman, WA) (Table 2).

ConA stimulated staining combinations were: CD4 & CD25, CD8 & CD25, TcR1-N6 (γδ T lymphocyte subpopulation) & CD25, CD25 only, CD4 & CD2, CD3 only, and TcR1-N6 only. PHA stimulated and unstimulated control combinations were: CD4 & CD25, CD8 & CD25 and TcR1-N6 & CD25. A cells only unstimulated control sample was also tested.

Stained cells were incubated for 20 min at 4° C. and washed three times with PBS at 520×g for 7 min at 25° C. The cells were resuspended again and stained with the secondary antibodies (Jackson ImmunoResearch, West Grove, Pa.) (Table 3). After 20 min incubation at 4° C., cells were washed three times as before and resuspended in 500 µl PBS with 1% paraformaldehyde. Subsequently a two-color flow analysis was performed on a Becton Dickinson FACScan flow cytometer, and the results were analyzed in FlowJo (Ver. 8.1.1; Tree Star, Inc., 1997-2006). Lymphocyte populations were identified by phenotypic and morphologic characterization and positive selection for $CD3^+$ expression.

For the LBT, 50 µl of PBMC ($5 \times 10^6$ cells/ml) in RPMI 1640 with 20% FCS and 1×antibiotic/antimycotic solution (Sigma, St. Louis, Mo.) was added in triplicate to a 96 well plate. Unstimulated control wells contained 100 µl of RPMI 1640. Stimulated sample wells contained 100 µl of ConA (final concentration of 6.7 µg/ml) or 100 µl of the M form of PHA diluted 1:200 in RPMI 1640. Plates were incubated at 37° C. in 5% $CO_2$ for 48 h, after which the cells were pulsed by adding 100 µl [$^3$H] thymidine diluted to 10 µCi/ml in RPMI 1640 to each well. After an additional incubation for 12-18 h at 37° C. in 5% $CO_2$, plates were placed at −20° C. for a minimum of 30 min. Cells were harvested using a Packard Filtermate 196 (PerkinElmer, Shelton, Conn.) and radioactivity was measured using a Packard Topcount Microplate Scintillation Counter (PerkinElmer, Shelton, Conn.).

The LBT data was analyzed using PROC UNIVARIATE in SAS. To remove background, the unstimulated control was subtracted from the mitogen stimulated value. The differences in proliferation for each calf pair (noni puree fed minus control) were computed for both ConA and PHA, at each of four time points (0, 3, 7, and 14 days). Normal quantile plots of the differences showed that they were not normally distributed; therefore Wilcoxon signed-rank tests were used to compare the median differences between the groups. The experiment-wise error rate was controlled at the 5% level within each mitogen treatment using a Bonferroni p-value correction.

For flow cytometry, separate analyses were done for ConA and PHA, for CD25 only, CD4 & CD25, CD8 & CD25, and TcR1-N6 & CD25 staining combinations. Each value was normalized to its baseline by subtracting the unsimulated, no treatment value or background from the mitogen stimulated value. The difference between the normalized values was taken between each calf pair, one receiving noni and the other not. This difference between noni and control calves was used as the response in a repeated measures ANOVA with a first-order autoregressive correlation structure to determine whether there was an effect of noni at each time, and/or a trend in the effect of noni over the time period of the study (0, 3, 7, and 14 days). P-values for mean differences between noni and control were corrected using the Bonferroni method; multiple comparisons between the mean differences at each time point were corrected using the Tukey Method. Residual analysis indicated no violation of the ANOVA assumptions of normality and constant variance. Significance was established at $p<0.05$.

Results and Discussion

Flow cytometry results showed a significant increase in percent expression of CD25 on $CD8^+$ T cells in response to ConA in noni-fed calves on day 3 of the study or approximately five days postpartum (p=0.036) (Table 5; FIG. 1). Though not statistically significant (p=0.11), there was also a noticeable increase in the expression of CD25 on $CD4^+$ T cells for noni fed calves stimulated by the same mitogen at the same time point. There were no significant differences with respect to the response to PHA within T cells subsets, nor were there any significant differences between noni fed and control calf results from the LBT.

Colostrum contains ingredients which influence the naive innate and adaptive immune responses. The immunoglobulins, leukocytes, and cytokines in colostrum are absorbed by the calf and play a major role in protecting the neonate through immune modulation.

In the present study we examined whether a phytochemical based immunomodulator, *Morinda citrifolia* (noni) puree, fed in conjunction with milk replacer could affect T cell function in neonatal calves in the first 2 weeks of life. To evaluate the effects of the noni puree on the immunity of newborn calves, T cell activation (CD25 expression) was measured with two-color flow cytometry. Cell proliferation in response to global (T cell) mitogens was also measured with a LBT.

Results showed immunoglobin competent calves receiving noni had a significant increase in $CD8^+$ T cells activation on day 3 of the study or approximately five days postpartum in response to ConA. There was also an increase in $CD4^+$ T cell activation for noni treated animals stimulated by the same mitogen on the same day.

The present invention contemplates that the significant increase in $CD8^+$ T cell activation and CD25 expression, may be due to the stimulating effects of noni on TNF-$\alpha$, IL-1$\beta$ and IFN-$\gamma$ found in the ingested colostrum. As the noni puree was administered in milk replacer, completely devoid of colostral cells, the present invention contemplates that noni had its effect on the maternal leukocytes previously absorbed by the calf. Noni-ppt initially stimulates macrophages to produce several cytokines, including IL-12, which induces NK cells and naïve T cells to differentiate into Th1 cells. These cells produce IFN-$\gamma$ and IL-2, which activates more Th cells, CD8+ CTL, NK cells, and INF-$\gamma$ and IL-5 production. Thus, by enhancing the activity of NK cells, noni-ppt is a potent stimulator of innate immunity. Workshop cluster $1^+$ $\gamma\delta$ T-cells, which are significantly more abundant in the peripheral blood of neonatal calves compared to adult animals, are stimulated by IL-12 and IL-18 to secrete large quantities of IFN-$\gamma$. Further, *Myco bacterium bovis* bacillus Calmette-Guerin-infected dendritic cells stimulated $CD3^-$ $CD8^+$ NK-like and $CD3^+$ $CD8^+$ T cell proliferation. The NK-like cells were the major population of IFN-$\gamma$ producers and may play a role in Th1-biased immune responses. These findings and the results of this study suggest that the CTL associated, Th1 cell-mediated, immune response may be due to direct or indirect stimulation by the noni puree on IFN-$\gamma$.

$CD4^+$ T cells have a slower rate of cell division in vitro and in vivo when compared to $CD8^+$ T cells. Additionally, MHC class I molecules, which interact with $CD8^+$ T cells, are expressed almost ubiquitously, while MHC class II molecules, which interact with $CD4^+$ T cells, are expressed on a more limited set of cells. This difference may provide $CD8^+$ T cells more opportunities to encounter antigens, thus reaching their activation threshold before $CD4^+$ T cells. This activation threshold difference may have contributed to the lack of statistical significance in activated $CD4^+$ T cells. The first phase of T cell response, the expansion stage, had no significant differences between calf groups as detected by the LBT. Experiments have shown proliferation of bovine mononuclear leukocytes stimulated by pokeweed mitogen remained relatively constant day 6 through 14 and peaked 12 d after seeding, while unstimulated control cells decreased over time with the lowest levels (<20%) 12 d after seeding. In this study, cells were counted approximately 4 days after seeding, which may not have allowed adequate incubation time to see a significant effect. In this experiment, no time course was executed, thus giving no information about possible trends in proliferation. Colostrum-fed calves have significantly higher proliferation counts than colostrum-deprived calves. As all calves in the study received adequate levels of colostrum, LBT results may have been altered by this effect, explaining why no significant difference was observed between control and noni-fed calves. Additionally, the samples had not been analyzed for lymphocyte composition, therefore it is difficult to determine if one cell subset was affected differently than another. Perhaps the lack of proliferation of one cell subset may have neutralized an increased response in another. A more appropriate test would have entailed fluorescent antibody labelling of each cell subset, staining cells with PKH or CFSE dye and analyzing proliferation via flow cytometry.

To summarize, we have shown that immunoglobin competent calves receiving noni had a significant increase in $CD8^+$ T cell activation on day 3 of the study or approximately five days postpartum in response to ConA when noni feeding is begun on the second day of life. We also showed a trend towards increased $CD4^+$ T cell activation for noni treated animals stimulated by the ConA on day 3.

What is claimed is:

1. A method for increasing $CD8^+$ T cell activation in an animal in need thereof, the method comprising the steps of:
   a. commencing feeding a dry food product to the animal when the animal is between 36 and 48 hours old, and
   b. continuing to feed the dry food product to the animal for a period of two weeks, wherein the dry food product is mixed with milk replacer and fed to the animal twice daily during the two-week period such that the consumption of the dry food product causes an increase in $CD8^+$ T cell activation in the animal by the third day of the two-week period and maintains an increased level of $CD8^+$ T cell activation during the remainder of the two-week period, wherein
   said dry food product comprises:
   *M. citrifolia* pasteurized fruit puree; and
   a *M. citrifolia* roasted seed product comprising one or more of: whole roasted noni seeds, whole roasted defatted noni seeds, roasted cracked noni seeds defatted, roasted cracked noni seeds, roasted ground noni seeds, roasted ground noni seeds defatted, roasted flaked noni defatted seeds, roasted flaked noni seeds, roasted extruded noni defatted seeds, roasted extruded noni seeds and extracts from roasted extruded noni seeds.

2. The method of claim 1, the dry food product further comprising an ingredient selected from a list comprising: glycosaminoglycans, hyaluronic acid, glucosamine HCl, glucosamine sulfate, chondroitin sulfate, essential amino acids, essential fatty acids, long chain fatty acids, omega 3 fatty acids, omega 6 fatty acids, macro minerals, plus micro minerals, peptides chains, branched chain amino acids.

3. The method of claim 1, wherein the dry food product further comprises an active ingredient selected from a group comprising quercetin, rutin, scopoletin, octoanoic acid, potassium, vitamin C, terpenoids, alkaloids, anthraquinones, nordamnacanthal, morindone, rubiandin, B-sitosterol, carotene, vitamin A, flavone glycosides, linoleic acid, Alizarin, amino acids, acubin, L-asperuloside, caproic acid, caprylic acid, ursolic acid, and putative proxeronines.

4. The method of claim 3, wherein said quercetin is present in an amount between about 0.1 and 10 percent by weight of the dry food product.

5. The method of claim 1, further comprising the steps of:
- collecting blood from the animal after the third day of the two-week period; and
- processing the blood to generate flow cytometry results to verify the increase in the level of $CD8^+$ T cell activation.

6. The method of claim 5, further comprising:
- feeding the dry food product to the animal beyond the two-week period when the flow cytometry results indicate that the level of $CD8^+$ T cell activation is below a threshold.

* * * * *